US008101169B2

(12) United States Patent
Chalberg, Jr. et al.

(10) Patent No.: US 8,101,169 B2
(45) Date of Patent: Jan. 24, 2012

(54) OCULAR GENE THERAPY USING AVALANCHE-MEDIATED TRANSFECTION

(75) Inventors: Thomas W. Chalberg, Jr., Redwood City, CA (US); Mark Blumenkranz, Portola Valley, CA (US); Daniel V. Palanker, Sunnyvale, CA (US); Alexander Vankov, Menlo Park, CA (US); Philip Huie, Jr., Cupertino, CA (US); Michael F. Marmor, Stanford, CA (US); Michele P. Calos, Burlingame, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 488 days.

(21) Appl. No.: 11/505,249

(22) Filed: Aug. 15, 2006

(65) Prior Publication Data

US 2007/0059835 A1 Mar. 15, 2007

Related U.S. Application Data

(63) Continuation of application No. 11/360,984, filed on Feb. 22, 2006.

(60) Provisional application No. 60/708,486, filed on Aug. 15, 2005, provisional application No. 60/655,559, filed on Feb. 23, 2005.

(51) Int. Cl.
*A61K 48/00* (2006.01)
(52) U.S. Cl. .................................. 424/93.2; 424/93.21
(58) Field of Classification Search ................. 424/93.2, 424/93.21
See application file for complete search history.

(56) References Cited

U.S. PATENT DOCUMENTS

| 5,019,034 A | 5/1991 | Weaver et al. |
| 5,028,597 A | 7/1991 | Kodama et al. |
| 5,128,257 A | 7/1992 | Baer |
| 5,304,486 A | 4/1994 | Chang |
| 5,318,514 A | 6/1994 | Hofmann |
| 5,389,069 A | 2/1995 | Weaver |
| 5,468,223 A | 11/1995 | Mir |
| 5,665,567 A | 9/1997 | Eichner et al. |
| 5,688,233 A | 11/1997 | Hofmann et al. |
| 5,749,847 A | 5/1998 | Zewert et al. |
| 5,964,726 A | 10/1999 | Korenstein et al. |
| 6,267,954 B1 | 7/2001 | Abitbol et al. |
| 6,352,535 B1 | 3/2002 | Lewis et al. |
| 6,384,301 B1 | 5/2002 | Martinell et al. |
| 6,500,449 B2 | 12/2002 | Abitbol et al. |
| 6,521,430 B1 | 2/2003 | Orwar et al. |
| 6,528,315 B2 | 3/2003 | Bureau et al. |
| 6,593,130 B1 | 7/2003 | Sen et al. |
| 6,627,421 B1 | 9/2003 | Unger et al. |
| 6,632,672 B2 | 10/2003 | Calos |
| 6,663,894 B2 | 12/2003 | Abitbol et al. |
| 6,678,558 B1 | 1/2004 | Dimmer et al. |
| 6,780,178 B2 | 8/2004 | Palanker et al. |
| 6,800,484 B2 | 10/2004 | Nolan et al. |
| 6,808,925 B2 | 10/2004 | Calos |
| 6,939,862 B2 | 9/2005 | Bureau et al. |
| 7,109,034 B2 | 9/2006 | Orwar et al. |
| 2003/0087859 A1 | 5/2003 | Kochanek et al. |
| 2004/0193097 A1 | 9/2004 | Hofmann et al. |
| 2005/0064578 A1 | 3/2005 | Muller-Hartmann et al. |
| 2005/0171039 A1 | 8/2005 | McSwiggen et al. |
| 2006/0115888 A1 | 6/2006 | Gamelin et al. |
| 2006/0123248 A1 | 6/2006 | Porter et al. |
| 2006/0269531 A1 | 11/2006 | Beeb et al. |

OTHER PUBLICATIONS

Mohan et al, (Progress in Retinal and Eye Research, 24: 537-559, 2005).*
Kumar-Singh et al (Vision Research 48: 1671-1680, 2008).*
Lund et al (J Leukoc Biol, 74: 151-160, 2003).*
Palanker et al, (Investigative Ophthalmology & Visual Science, 42(11): 2673-2678, 2001).*
Lai, Chooi-May, et al., "Long-Term Evaluation of AAV-Mediated sFlt-1 Gene Therapy for Ocular Neovascularization in Mice and Monkeys," Mol. Therapy, vol. 12(4): 659-668 (Oct. 2005; available online Jul. 14, 2005).
Chalberg, T.W., et al., "Novel Physical Methods for Nonviral DNA Transfer to Rabbit Retina," Molecular Therapy, vol. 11(1): Abstract 770 (May 2005).
Hageman, G.S. et al., "A common haplotype in the complement regulatory gene factor H *HF1/CFH) predisposes individuals to age-related macular degeneration," PNAS, vol. 102(20): 7227-7232 (May 17, 2005).
International Search Report issued for PCT/US06/32249, dated Mar. 2, 2010 (1 page).
International Search Report issued for PCT/US06/37010 dated Aug. 5, 2008 (1 page).
Borras T. "Recent developments in ocular gene therapy," Experimental Eye Research, 76(6): 643-652 (2003).
Chalberg TW et al. "phiC31 integrase confers genomic integration and long-term transgene expression in rat retina," Investigative Ophthalmology & Visual Science, 46(6): 2140-2146 (2005).
Miller JM et al., "Precision and safety of the pulsed electron avalanche knife in vitreoretinal surgery," Archives of Ophthalmology, 121(6): 871-877 (2003).

(Continued)

*Primary Examiner* — Thaian N Ton
*Assistant Examiner* — Magdalene K Sgagias
(74) *Attorney, Agent, or Firm* — K&L Gates LLP; Ann-Louise Kerner

(57) ABSTRACT

The present invention provides a method of treating an ocular disease in a subject. In a first step, a nucleic acid is introduced into cells or a tissue. The nucleic acid is introduced by electron avalanche transfection. With this technique, a high electric field induces a vapor bubble and plasma discharge between an electrode and the surrounding medium. The formation of a vapor bubble generates mechanical stress. Plasma discharge through the ionized vapor in the bubble enables connectivity between the electrode and the surrounding medium, so that mechanical stress and electric field are applied simultaneously, which results in permeabilization of the cells or tissue. This permeabilization in turn allows the nucleic acid to enter the cell or tissue. Cells or tissue containing the nucleic acid are then transplanted into an ocular region of the subject.

20 Claims, 10 Drawing Sheets

OTHER PUBLICATIONS

Semkova I et al., "Autologous transplantation of genetically modified iris pigment epithelial cells: a promising concept for the treatment of age-related macular degeneration and other disorders of the eye," PNAS (USA), 99(20): 13090-13095 (2002).

Tamai M, "Progress in pathogenesis and therapeutic research in retinitis pigmentosa and age-related macular degeneration," Nippon Ganka Gakkai Zasshi, 108(12): 750-751 (2004). (English translation of abstract submitted).

* cited by examiner

SEQUENCE LISTING

<160> NUMBER OF SEQ ID NOS: 1

<210> SEQ ID NO 1
<211> LENGTH: 7166
<212> TYPE: DNA
<213> ORGANISM: Artificial
<220> FEATURE:
<223> OTHER INFORMATION: Nucleotide sequence for the circular construct
      shown in FIG. 7

<400> SEQUENCE: 1

| | | | | | |
|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggag | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catggtgatg | cggttttggc | agtacatcaa | tgggcgtgga | tagcggtttg | actcacgggg | 420 |
| atttccaagt | ctccacccca | ttgacgtcaa | tgggagtttg | ttttggcacc | aaaatcaacg | 480 |
| ggactttcca | aaatgtcgta | acaactccgc | cccattgacg | caaatgggcg | gtaggcgtgt | 540 |
| acggtgggag | gtctatataa | gcagagctgg | tttagtgaac | cgtcagatcc | gctagcgcta | 600 |
| ccggactcag | atctcgagct | caagcttcga | attctgcagt | cgacggtacc | gcgggcccgg | 660 |
| tcgctttaag | aaaggagtag | ctgtaatctg | aagcctgctg | gacgctggat | tagaaggcag | 720 |
| caaaaaaagc | tctgtgctgg | ctggagcccc | tcagtgtgc | aggcttagag | ggactaggct | 780 |
| gggtgtggag | ctgcagcgta | tccacaggcc | ccaggatgca | ggccctggtg | ctactcctct | 840 |
| gcattggagc | cctcctcggg | cacagcagct | gccagaaccc | tgccagcccc | cggaggagg | 900 |
| gctccccaga | ccccgacagc | acaggggcgc | tggtggagga | ggaggatcct | tcttcaaag | 960 |
| tccccgtgaa | caagctggca | gcggctgtct | ccaacttcgg | ctatgacctg | tacgggtgc | 1020 |
| gatccagcac | gagccccacg | accaacgtgc | tcctgtctcc | tctcagtgtg | gccacggccc | 1080 |
| tctcggccct | ctcgctggga | gcggagcagc | gaacagaatc | catcattcac | cgggctctct | 1140 |
| actatgactt | gatcagcagc | ccagacatcc | atggtaccta | taggagctc | cttgacacgg | 1200 |
| tcactgcccc | ccagaagaac | ctcaagagtg | cctcccggat | cgtctttgag | aagaagctgc | 1260 |
| gcataaaatc | cagctttgtg | gcacctctgg | aaaagtcata | tgggaccagg | cccagagtcc | 1320 |
| tgacgggcaa | ccctcgcttg | gacctgcaag | agatcaacaa | ctgggtgcag | gcgcagatga | 1380 |
| aagggaagct | cgccaggtcc | acaaaggaaa | ttcccgatga | gatcagcatt | ctccttctcg | 1440 |
| gtgtggcgca | cttcaagggg | cagtgggtaa | caaagtttga | ctccagaaag | acttccctcg | 1500 |
| aggatttcta | cttggatgaa | gagaggaccg | tgagggtccc | catgatgtcg | gaccctaagg | 1560 |
| ctgttttacg | ctatggcttg | gattcagatc | tcagctgcaa | gattgcccag | ctgcccttga | 1620 |
| ccggaagcat | gagtatcatc | ttcttcctgc | ccctgaaagt | gacccagaat | ttgaccttga | 1680 |
| tagaggagag | cctcacctcc | gagttcattc | atgacataga | ccgagaactg | aagaccgtgc | 1740 |
| aggcggtcct | cactgtcccc | aagctgaagc | tgagttatga | aggcgaagtc | accaagtccc | 1800 |
| tgcaggagat | gaagctgcaa | tccttgtttg | attcaccaga | ctttagcaag | atcacaggca | 1860 |
| aacccatcaa | gctgactcag | gtggaacacc | gggctggctt | tgagtggaac | gaggatgggg | 1920 |
| cgggaaccac | ccccagccca | gggctgcagc | ctgcccacct | caccttcccg | ctggactatc | 1980 |

```
accttaacca gcctttcatc ttcgtactga gggacacaga cacaggggcc cttctcttca    2040
ttggcaagat tctggacccc aggggcccct aatatcccag tttaatattc caataccta     2100 gaagaaaacc cgagggacag cagattccac aggacacgaa ggctgcccct gtaaggtttc    2160
aatgcataca ataaaagagc tttatcccta acttctgtta gggatccgcc cctctccctc    2220 cccccccct  aacgttactg gccgaagccg cttggaataa ggccggtgtg cgtttgtcta    2280
tatgttattt tccaccatat tgccgtcttt tggcaatgtg agggcccgga aacctggccc    2340
tgtcttcttg acgagcattc ctaggggtct ttcccctctc gccaaaggaa tgcaaggtct    2400
gttgaatgtc gtgaaggaag cagttcctct ggaagcttct tgaagacaaa caacgtctgt    2460
agcgacccct tgcaggcagc ggaaccccc  acctggcgac aggtgcctct gcggccaaaa    2520
gccacgtgta taagatacac ctgcaaaggc ggcacaaccc cagtgccacg ttgtgagttg    2580
gatagttgtg aaagagtca  aatggctctc ctcaagcgta ttcaacaagg ggctgaagga    2640
tgcccagaag gtaccccatt gtatgggatc tgatctgggg cctcggtgca catgctttac    2700
atgtgtttag tcgaggttaa aaaaacgtct aggcccccg  aaccacgggg acgtggtttt    2760
cctttgaaaa acacgatgat aatatggcca caaccatggt gagcaagggc gaggagctgt    2820
tcaccggggt ggtgcccatc ctggtcgagc tggacggcga cgtaaacggc cacaagttca    2880
gcgtgtccgg cgagggcgag ggcgatgcca cctacggcaa gctgaccctg aagttcatct    2940
gcaccaccgg caagctgccc gtgccctggc ccaccctcgt gaccaccctg acctacggcg    3000
tgcagtgctt cagccgctac cccgaccaca tgaagcagca cgacttcttc aagtccgcca    3060
tgcccgaagg ctacgtccag gagcgcacca tcttcttcaa ggacgacggc aactacaaga    3120
cccgcgccga ggtgaagttc gagggcgaca cccctggtgaa ccgcatcgag ctgaagggca    3180
tcgacttcaa ggaggacggc aacatcctgg ggcacaagct ggagtacaac tacaacagcc    3240
acaacgtcta tatcatggcc gacaagcaga agaacggcat caaggtgaac ttcaagatcc    3300
gccacaacat cgaggacggc agcgtgcagc tcgccgacca ctaccagcag aacacccca    3360 tcggcgacgg ccccgtgctg ctgcccgaca accactacct gagcacccag tccgccctga    3420
gcaaagaccc caacgagaag cgcgatcaca tggtcctgct ggagttcgtg accgccgccg    3480
ggatcactct cggcatggac gagctgtaca agtaaagcgg ccgcgactct agatcataat    3540
cagccatacc acatttgtag aggttttact tgctttaaaa aacctcccac acctccccct    3600
gaacctgaaa cataaaatga atgcaattgt tgttgttaac ttgtttattg cagcttataa    3660
tggttacaaa taaagcaata gcatcacaaa tttcacaaat aaagcatttt tttcactgca    3720
ttctagttgt ggtttgtcca aactcatcaa tgtatcttaa ggcgtaaatt gtaagcgtta    3780
atattttgtt aaaattcgcg ttaaattttt gttaaatcag ctcatttttt aaccaatagg    3840
ccgaaatcgg caaaatccct tataaatcaa agaatagac  cgagataggg ttgagtgttg    3900
ttccagtttg gaacaagagt ccactattaa agaacgtgga ctccaacgtc aaagggcgaa    3960
aaaccgtcta tcagggcgat ggcccactac gtgaaccatc accctaatca agttttttgg    4020
ggtcgaggtg ccgtaaagca ctaaatcgga acccctaaagg gagccccga  tttagagctt    4080 gacggggaaa gccggcgaac gtggcgagaa aggaagggaa gaaagcgaaa ggagcgggcg    4140
ctagggcgct ggcaagtgta gcggtcacgc tgcgcgtaac caccacaccc gccgcgctta    4200
atgcgccgct acagggcgcg tcaggtggca ctttcgggg  aaatgtgcgc ggaaccccta    4260
tttgtttatt tttctaaata cattcaaata tgtatccgct catgagacaa taaccctgat    4320
aaatgcttca ataatattga aaaggaaga  gtcctgaggc ggaaagaacc agctgtggaa    4380
```

```
tgtgtgtcag ttagggtgtg aaagtccccc aggctcccca gcaggcagaa gtatgcaaag      4440
catgcatctc aattagtcag caaccaggtg tggaaagtcc ccaggctccc cagcaggcag      4500
aagtatgcaa agcatgcatc tcaattagtc agcaaccata gtcccgcccc taactccgcc      4560
catcccgccc ctaactccgc ccagttccgc ccattctccg ccccatggct gactaatttt      4620
ttttatttat gcagaggccg aggccgcctc ggcctctgag ctattccaga agtagtgagg      4680
aggctttttt ggaggcctag gcttttgcaa agatcgatca agagacagga tgaggatcgt      4740
ttcgcatgat tgaacaagat ggattgcacg caggttctcc ggccgcttgg gtggagaggc      4800
tattcggcta tgactgggca acagacaa tcggctgctc tgatgccgcc gtgttccggc       4860
tgtcagcgca ggggcgcccg gttcttttg tcaagaccga cctgtccggt gccctgaatg      4920
aactgcaaga cgaggcagcg cggctatcgt ggctggccac gacgggcgtt ccttgcgcag     4980
ctgtgctcga cgttgtcact gaagcggaa gggactggct gctattgggc gaagtgccgg      5040
ggcaggatct cctgtcatct caccttgctc ctgccgagaa agtatccatc atggctgatg     5100
caatgcggcg gctgcatacg cttgatccgg ctacctgccc attcgaccac caagcgaaac     5160
atcgcatcga gcgagcacgt actcggatgg aagccggtct tgtcgatcag gatgatctgg     5220
acgaagagca tcaggggctc gcgccagccg aactgttcgc caggctcaag gcgagcatgc     5280
ccgacggcga ggatctcgtc gtgacccatg gcgatgcctg cttgccgaat atcatggtgg     5340
aaaatggccg cttttctgga ttcatcgact gtggccggct gggtgtggcg gaccgctatc     5400
aggacatagc gttggctacc cgtgatattg ctgaagagct tggcggcgaa tgggctgacc     5460
gcttcctcgt gctttacggt atcgccgctc ccgattcgca gcgcatcgcc ttctatcgcc     5520
ttcttgacga gttcttctga gcgggactct ggggttcgaa atgaccgacc aagcgacgcc     5580
caacctgcca tcacgagatt tcgattccac cgccgccttc tatgaaaggt tgggcttcgg     5640
aatcgttttc cgggacgccg gctggatgat cctccagcgc ggggatctca tgctggagtt     5700
cttcgcccac cctaggggga ggctaactga acacggaag gagacaatac cggaaggaac      5760
ccgcgctatg acggcaataa aaagacagaa taaaacgcac ggtgttgggt cgtttgttca     5820
taaacgcggg gttcggtccc agggctggca ctctgtcgat accccacaat tcggcttggc     5880
tgtcgacatg cccgccgtga ccgtcgagaa cccgctgacg ctgccccgcg tatccgcacc     5940
cgccgacgcc gtcgcacgtc ccgtgctcac cgtgaccacc gcgcccagcg gtttcgaggg     6000
cgagggcttc ccggtgcgcc gcgcgttcgc cgggatcaac taccgccacc tcgacccgtt     6060
catcatgatg gaccagatgg gtgaggtgga gtacgcgccc ggggagccca agggcacgcc     6120
ctggcacccg caccgcggct tcagaccgt gacctacatc gtcgacggta cctggaattc      6180
caccgagacc ccattggggc caatacgccc gcgtttcttc cttttcccca ccccaccccc     6240
caagttcggg tgaaggccca gggctcgcag ccaacgtcgg ggcggcaggc cctgccatag     6300
cctcaggtta ctcatatata ctttagattg atttaaaact tcatttttaa tttaaaagga     6360
tctaggtgaa gatccttttt gataatctca tgaccaaaat cccttaacgt gagttttcgt     6420
tccactgagc gtcagacccc gtagaaaaga tcaaaggatc ttcttgagat ccttttttc      6480 tgcgcgtaat ctgctgcttg caaacaaaaa aaccaccgct accagcggtg gtttgtttgc     6540
cggatcaaga gctaccaact cttttccga aggtaactgg cttcagcaga gcgcagatac      6600
caaatactgt ccttctagtg tagccgtagt taggccacca cttcaagaac tctgtagcac     6660
cgcctacata cctcgctctg ctaatcctgt taccagtggc tgctgccagt ggcgataagt     6720
cgtgtcttac cgggttggac tcaagacgat agttaccgga taaggcgcag cggtcgggct     6780
```

```
gaacgggggg ttcgtgcaca cagcccagct tggagcgaac gacctacacc gaactgagat    6840
acctacagcg tgagctatga gaaagcgcca cgcttcccga agggagaaag gcggacaggt    6900
atccggtaag cggcagggtc ggaacaggag agcgcacgag ggagcttcca gggggaaacg    6960
cctggtatct ttatagtcct gtcgggtttc gccacctctg acttgagcgt cgattttttgt   7020 gatgctcgtc aggggggcgg agcctatgga aaaacgccag caacgcggcc tttttacggt    7080
tcctggcctt ttgctggcct tttgctcaca tgttctttcc tgcgttatcc cctgattctg    7140
tggataaccg tattaccgcc atgcat                                          7166
```

OCULAR GENE THERAPY USING AVALANCHE-MEDIATED TRANSFECTION

CROSS-REFERENCE TO RELATED APPLICATIONS

This application claims priority from U.S. Provisional Patent Application No. 60/708,486, filed Aug. 15, 2005 and from U.S. patent application Ser. No. 11/360,984, filed Feb. 22, 2006, which claims priority from U.S. Provisional Patent Application No. 60/655,559, filed Feb. 23, 2005, all of which are incorporated herein by reference.

STATEMENT REGARDING FEDERALLY SPONSORED RESEARCH OR DEVELOPMENT

This invention was made with Government support under contract HL068112 awarded by the National Institute of Health. The Government has certain rights in this invention.

FIELD OF THE INVENTION

The present invention relates generally to medicine. More particularly, the present invention relates to a method of treating ocular diseases with gene therapy using avalanche-mediated transfection to genetically modify cells or tissue.

BACKGROUND

There are many ocular diseases that affect vision. Diseases of the conjunctiva and cornea, cataracts, uveal diseases, retinal diseases, loss of central acuity and visual field abnormalities and diseases of Bruch's membrane are a few examples. Age-related macular degeneration is a "wet" form of age-related macular degeneration, choroidal neovascularization leads to progressive disease and vision loss.

Current therapeutics for treatment of many ocular conditions require the need for frequent intravitreal administration. Therapies involving delivery of proteins or aptamers are examples of such approaches, with the drawback that proteins and aptamers have short half-lives and require intravitreal administration every 4-6 weeks for life for maximal efficacy. Gene therapy approaches are potentially more long-term, with the possibility of lasting many months or years. Gene therapy can be in vivo, involving delivery of therapeutic genes directly to the tissue of interest, or can be ex vivo, where tissue selected for use is treated outside the body prior to implantation. The art has long sought gene therapy treatment methods that are safe for the patient and therapeutically viable.

One of the important factors in the efficacy and safety of gene therapy is the method used to introduce DNA into a cell. Viral vectors, such as retroviruses and adenoviruses, enable high expression of the introduced DNA but have safety concerns. Non-viral methods, such as liposomes, have low host immunogenicity but tend to suffer from inefficient DNA delivery to cells. Accordingly, there is a need in the art for new methods of introducing DNA into cells and tissues for the purpose of gene therapy.

SUMMARY OF THE INVENTION

The present invention provides a method of treating an ocular disease in a subject. In a first step, a nucleic acid is introduced into cells or a tissue. The nucleic acid is introduced by electron avalanche-mediated transfection. With this technique, a high electric field induces a vapor bubble and plasma discharge between an electrode and the surrounding medium. The formation of a vapor bubble generates mechanical stress. Plasma discharge through the ionized vapor in the bubble enables connectivity between the electrode and the surrounding medium, so that the mechanical stress and electric field are applied simultaneously, which results in permeabilization of the cells or tissue. This permeabilization in turn allows the nucleic acid to enter the cell or tissue. Cells or tissue containing the nucleic acid are then transplanted into an ocular region of the subject.

Cells and tissue according to the present invention are preferably autologous (i.e. from the subject), or allogeneic (i.e. from an individual of the same species). In the case of cells, the cells may be primary cells or cell lines. Preferred primary cells are conjunctival fibroblasts, scleral cells, or epithelial cells. Preferred cell lines are fibroblast cell lines or muscle cell lines. Preferred tissues are conjunctival tissue and scleral tissue. The cells or tissue may be cultured prior to transplantation. Alternatively, or in addition, the cells or tissue may be placed in a cage, such as a polymeric cage, or a scaffold or matrix to support the growth of the cells.

In a preferred embodiment, the nucleic acid is DNA. The DNA may encode, for example, a therapeutic protein or an RNAi cassette, such as a short-hairpin RNA (shRNA). Alternatively, the DNA may be used for modifying an endogenous gene. For example, the DNA may be an oligonucleotide used for gene repair, or may be used for homologous recombination with an endogenous gene, for the purpose of modifying the gene. Modifications include, for example, modifying expression levels of the gene and/or replacing a mutant gene with a wild-type copy of the gene. In a particularly preferred embodiment, the nucleic acid is part of a plasmid. The plasmid may, in addition to a therapeutic gene, contain a marker gene. In order to obtain genomic integration, the plasmid may contain integration elements, such as a phiC31 attB site or inverted repeats recognized by transposases such as Sleeping Beauty. In this case, a source of phiC31 integrase or a transposase would also be provided.

Genetically-modified cells or tissue may be transplanted into any ocular region of the subject. Preferred regions are the choroid, vitreous humor, retinal pigment epithelium, near the macula, and behind the sclera. In the case of a macular region, the ocular region may be epiretinal to the macula, subretinal to the macula, or intra-retinal to the macula. In the case of the vitreous humor, the ocular region is preferably a region of the vitreous humor near the pars plana.

Any ocular disease may be treated according to the present invention. Examples include, but are not limited to, age-related macular degeneration, choroidal neovascularization, retinal degeneration, glaucoma, diabetic retinopathy, and retinal dystrophies. Similarly, any subject may be treated according to the present invention. Preferred subjects are humans and non-human mammals.

BRIEF DESCRIPTION OF THE FIGURES

The present invention together with its objectives and advantages will be understood by reading the following description in conjunction with the drawings, in which.

DETAILED DESCRIPTION OF THE INVENTION

Avalanche Method

Figure 1:
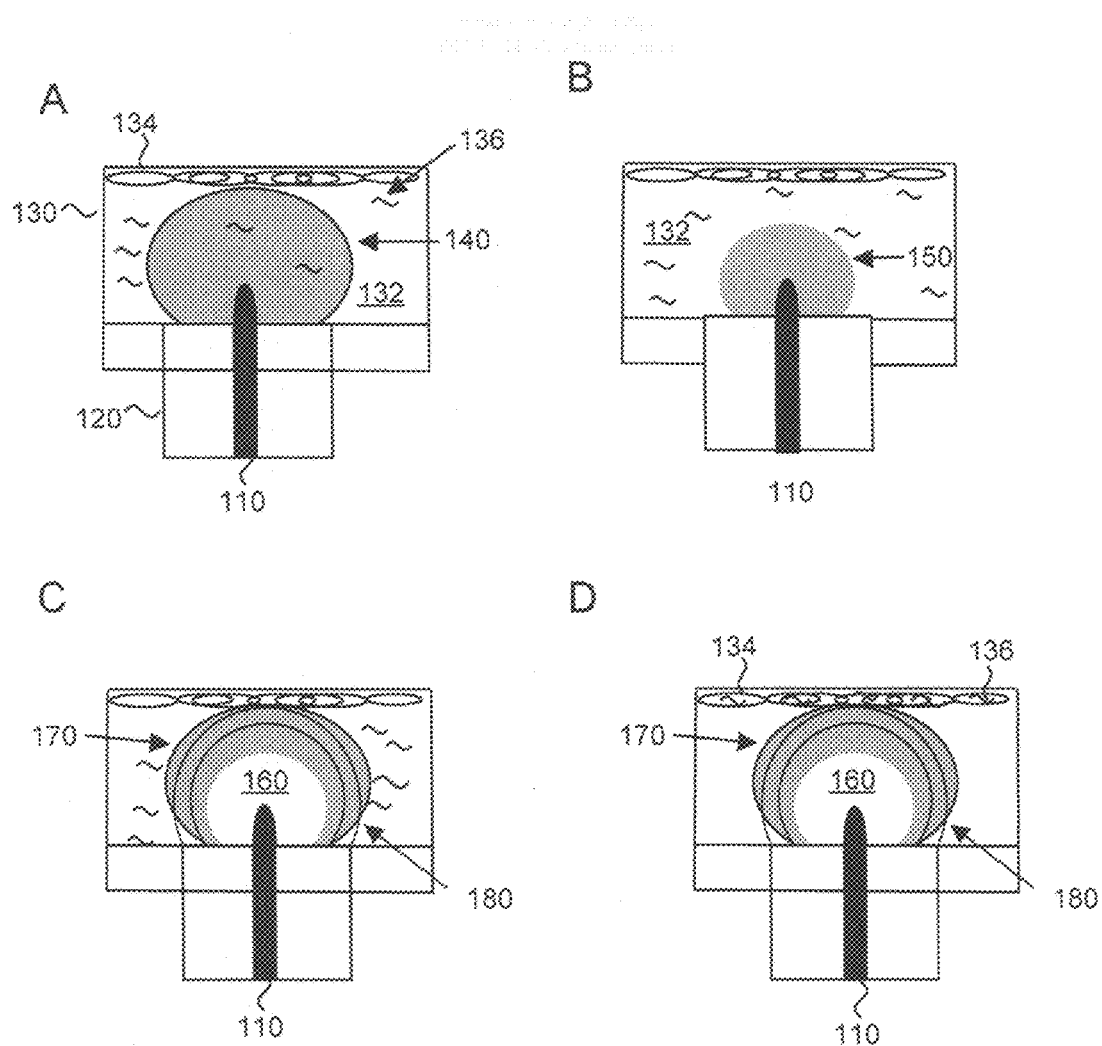
FIG. 1 shows the avalanche method according to the present invention.

The present invention provides an ex vivo gene therapy method based on a novel method of introducing DNA into cells called the avalanche method. When sufficiently high voltage is applied to an electrode, a mechanical stress wave synchronized with a pulse of electric current can be produced and applied to cells or tissue, as shown in FIG. 1. FIG. 1A-C shows three stages that occur when a high voltage is applied to an electrode 110 covered by insulation 120. Electrode 110 is situated in tissue culture well 130, with conductive liquid medium 132, cells 134, and nucleic acid 136. (While cells are pictured in this figure, tissue could also be used). When a voltage is first applied to electrode 110, (FIG. 1A), an electric field 140 is generated around the un-insulated portion of electrode 110. If the electric field in the medium is sufficiently high, generated Joule heat leads to rapid vaporization of liquid medium 132 in the areas adjacent to electrode 110, resulting in generation of a vapor bubble 150 (FIG. 1B). As soon as vapor bubble 150 is formed, it disconnects the surface of electrode 110 from conductive medium 132, so that the electric current stops flowing, and the electric field on the target cells is terminated. To overcome this difficulty, the vapor in the bubble can be ionized to form ionized vapor 160, which restores the electrical conductivity, as shown in FIG. 1C. Ionized vapor 160, also known as plasma, forms a kind of virtual electrode with electric field 170. During this process, the formation of the vapor bubble, and its subsequent collapse, causes a propagating shock wave through the medium, exposing the cells or tissue to mechanical stress 180. The combination of the shock wave and the electric field leads to permeabilization of cells 132, such that nucleic acid 136 may enter cells 132 (FIG. 1D). Highlighting the role of the plasma-mediated electric discharge, the inventors have named this technique electron avalanche-mediated transfection, or, for simplicity, the avalanche method.

Figure 2:
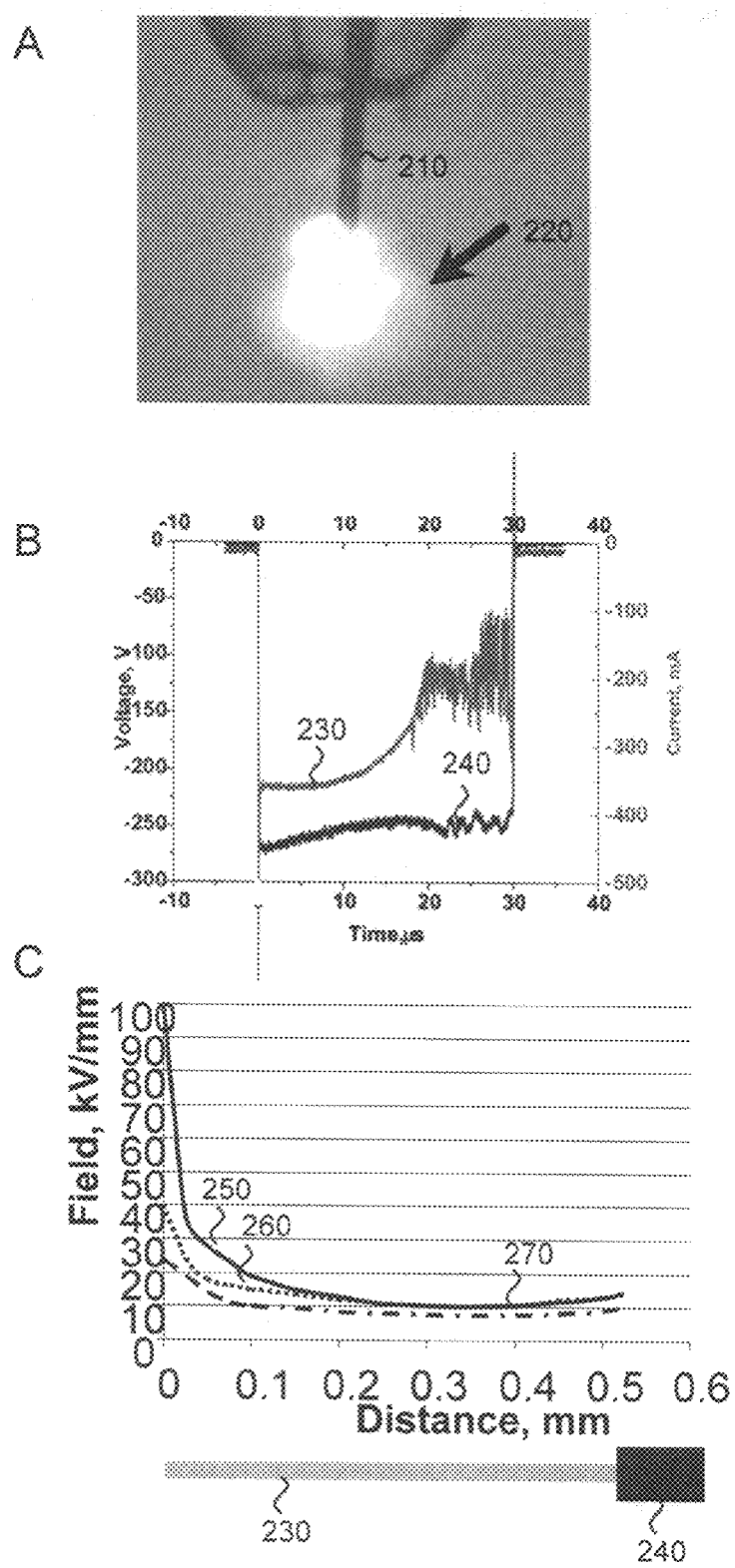
FIG. 2 shows the use of the avalanche method according to the present invention with wire electrodes.

The process described in FIG. 1 works when the electrode produces a relatively uniform electric field. Alternatively, electrodes with a very uneven electric field may be used, so that the vapor cavity formed at the apex does not cover the whole surface of the electrode with a lower electric field. This way the electric current to the medium will not be completely disconnected. One example of an electrode geometry with a non-uniform electric field is a cylindrical probe, such as a wire, with a sharp end. FIG. 2A shows an image of a wire electrode 210 producing a plasma discharge 220. As can be seen from FIG. 2A, the plasma discharge is clearly visible. It is also clearly audible. FIG. 2B shows current 230 and voltage 240 versus time when a voltage is applied to a wire probe. In this particular example, the wire probe was 50 μm in diameter and electrical pulses of up to 600 V were used to produce an electric field at the tip of the wire of about 30 kV/cm. However, these parameters may be varied. FIG. 2B shows that when a voltage is applied to such a probe, the initial 20 μs of the waveform exhibits reduction of the current due to beginning of vaporization. This is followed by stabilization of conductivity following ionization of the vapor cavity. The ionized vapor cavity serves as a transient electrode, which can greatly exceed the size of the probe, as shown in FIG. 2A. As a result, the distribution of the electric field becomes much more uniform than the one generated initially on the small wire electrode, thus leading to more uniform electroporation of the target cells or tissue.

FIG. 2C shows, for different diameters of electrodes, the field strength (kV/mm) along the length of electrode 230 covered by insulator 240. The electrode diameter indicated by the solid line 250 is 10 μm, the dotted line 260 is 25 μm, and the dashed line 270 is 50 μm. In this particular experiment, 600 V was applied to the electrode. FIG. 2C shows that for a cylindrical electrode with a sharp tip, there is a rapid decrease in electric field as one moves farther away from the tip of the electrode. Thus, the strength of the electric field at the apex of the electrode can be varied by changing the electrode diameter.

Figure 3:
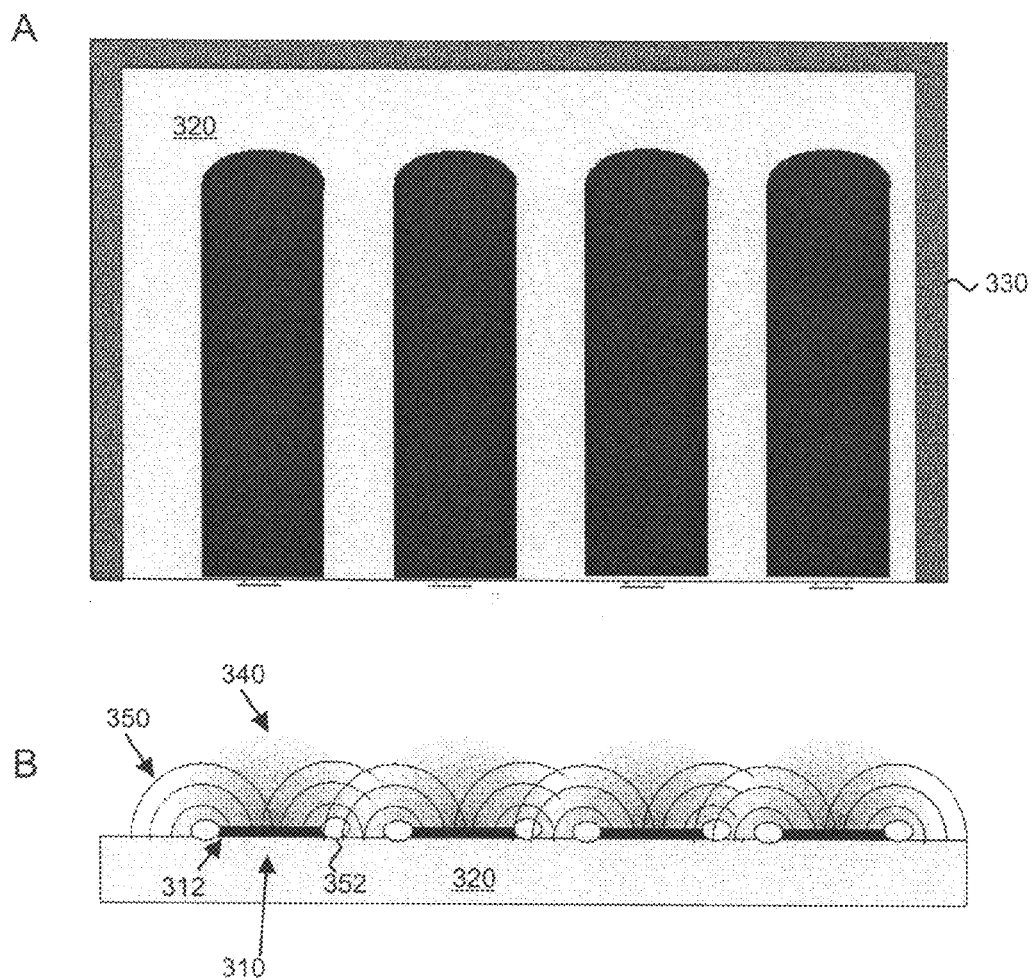
FIGS. 3-6 show examples of electrode geometries suitable for practicing the avalanche method according to the present invention.

Various types of probes may be used according to the present invention. FIG. 3 shows a version of a probe in which active electrodes 310 are plated on a substrate 320. FIG. 3A shows a top view and FIG. 3B shows a side view of the probe. In this probe, substrate 320 is surrounded by return electrode 330. The pattern of active electrodes 310 on substrate 320 forms the necessary proportion between electric field 340 and mechanical stress wave 350 due to plasma discharge 352. The probe in FIG. 3 has a singularity of the electric field 340 at the edges 312 of active electrodes 310. Singularities serve as ignition points for plasma discharge 352 and generation of mechanical stress wave 350. In FIG. 1, plasma occupies the whole volume of the vapor cavity. In contrast, in FIG. 3, the electric field at the edges of the thin electrode is much higher than in front of its flat part so vaporization and ionization will occur (or start) primarily there. This implementation is simple and inexpensive, but it does not provide the flexibility to control mechanical and electric pulse parameters separately.

Figure 4:
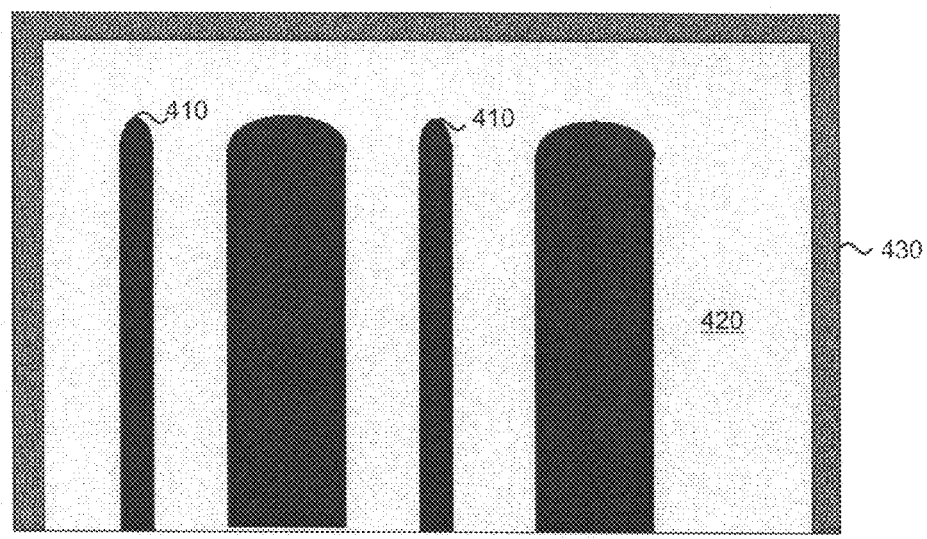
Figure 4:
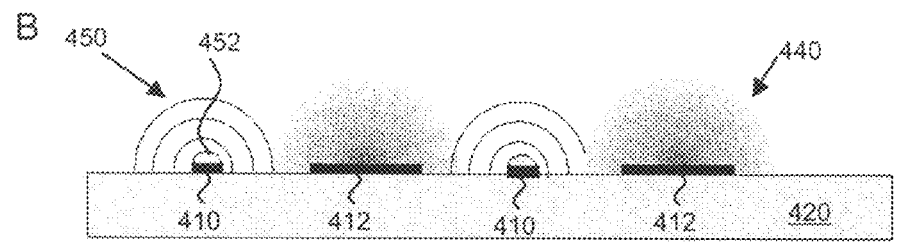

Another probe implementation, which allows separate control of mechanical stress wave 450 and electric field 440, is shown in FIG. 4. (FIG. 4A is a top view, FIG. 4B is a side view). In this implementation, two types of active electrodes, 410 and 412, are patterned on substrate 420, with return electrode 430 surrounding substrate 420. Electrodes 412 may be driven to generate an electric field 440, while electrodes 410 may be driven to generate plasma 452 and mechanical stress wave 450. (Plasma 454 also generates an accompanying electric field, not shown). Separate control of the amplitude of stress wave and electric field might be desirable for optimization of permeabilization. Generating them on the same electrode will make these values mutually dependent, while generation on two separate electrodes may provide independent control of these phenomena.

Figure 5:
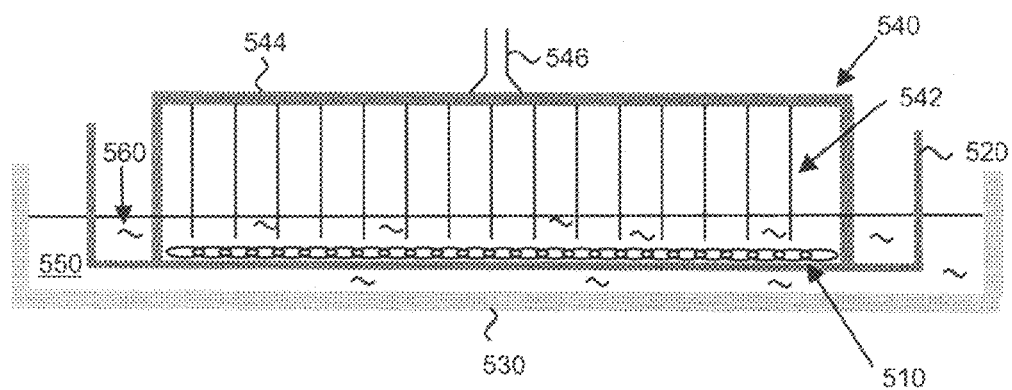

FIG. 5 shows an example of a transfection device suitable for molecular delivery of nucleic acid to adherent cells or tissue according to the present invention. In this arrangement, cells 510 are growing on an adherent surface 520 placed in a nonporous substrate 530, such as a tissue culture plate. Adherent surface 520 may be, for example, a tissue culture insert made of porous material such as polycarbonate. Cells could also be grown directly on nonporous substrate 530. A gelatinous matrix and/or feeder layer may also be present (not shown). A probe 540 with pillar electrodes 542, return electrode 544, and connection 546 to a voltage source (not shown) is brought into a solution 550 containing nucleic acid 560. Pillar electrodes 542 are positioned a finite distance from cells 510, e.g. about 1 mm. This finite distance is preferably in the range of about 0.5 mm to about 2 cm. In the embodiment shown, the return electrode 544 extends beyond pillar electrodes 542 a distance equal to this finite distance such that the finite distance is defined when the return electrode 544 is touching adherent surface 520. However, this distance could be defined by any substance. In addition, pillar electrodes 542 are preferably about 0.5 mm to about 2 cm apart.

Figure 6:
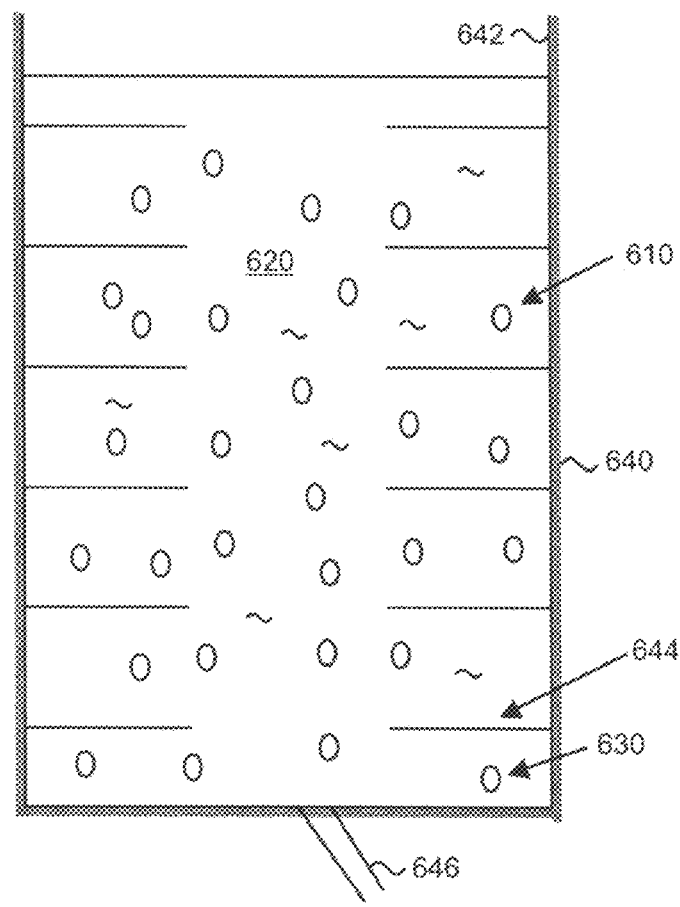

FIG. 6 shows an example of a transfection device suitable for molecular delivery of nucleic acid to cells or tissue in solution according to the present invention. In this arrangement, cells or tissue 610 are suspended in solution 620 with nucleic acids 630 in cuvette 640. Cuvette 640 contains return electrode 642, pillar electrodes 644, and connection 646 to a voltage source (not shown). In this design, pillar electrodes 644 are preferably between about 0.5 mm and about 2 cm apart to provide adequate coverage of the solution volume. In this arrangement, the pillar electrodes could be simultaneously or alternately active.

Regardless of probe design, to produce a strong stress wave, the electric field on the electrode surface should be sufficient for rapid vaporization of the liquid medium. In addition, to maintain connectivity, the electric field should be high enough to induce ionization of the vapor. In this way, both a mechanical stress wave and an electric field can be synchronized, with maximal intensity at the surface of the electrode. In addition to these concerns, the plasma discharge must be controlled in order to maximize transfection efficiency and minimize cell death.

Several parameters may be varied to meet the above requirements, such as electric field strength, applied voltage, pulse duration, number of pulses, frequency, etc. The actual values of these parameters will depend on the specific electrode geometry. In general, however, applied voltages are preferably in the range of about 1 V to about 10 kV, more preferably between about 100 V and about 1 kV. Applied voltage preferably results in an electric field between about 1 to about 100 kV/cm, more preferably about 10 to about 50 kV/cm, and most preferably about 30 kV/cm. Pulse duration is preferably in the range of about 1 ns to about 100 ms, more preferably between about 100 ns and about 1 ms. Either monophasic or biphasic pulses are suitable for the purposes of the present invention. However, biphasic pulses are preferred as they lead to less gas formation, nerve and muscle response, and electrode erosion. Any number of pulses may be used according to the present invention. The number of pulses is preferably between about 1 and 100, more preferably between about 1 and 50. When multiple pulses are used, the frequency of pulses should be in the range of about 0.1 Hz to about 1 kHz. Preferably, the frequency is less than about 1 kHz to prevent heat accumulation.

Cells and Tissues

Any cell or tissue may be suitable for practicing the invention. Examples include primary cells, primary tissues, and cell lines. Preferred cells include conjunctival fibroblasts, epithelial cells and scleral cells. Preferred tissues include conjunctival tissue and scleral tissue. Preferred cell lines include fibroblast cell lines and muscle cell lines. The cells and tissue are preferably autologous or allogeneic.

In one embodiment, the method of the present invention involves obtaining tissue from a subject having or at risk of developing an undesirable eye condition. The condition can range from a minor or nuisance condition, such as dry eye, to a more serious disease with possible vision loss, such as age-related macular degeneration. Under the care of a skilled medical provider, tissue from the patent is harvested in an invasive, minimally invasive, or non-invasive procedure, the degree of invasiveness dictated, in part, by the tissue to be harvested. Candidate tissues are preferably those capable of transfection and production of a protein, and that are capable of survival in the transplanted environment.

In one aspect of this embodiment, tissue is harvested from the eye and it is contemplated that any tissue in the eye may be harvested in any feasible manner. For example, conjunctival fibroblasts can be excised from the eye by, for example, anesthetizing the conjunctiva with a topical agent such as propraracaine, cleansing and preparing the area with betadine or another cidal agent, and then taking a snip biopsy with a pair of toothed forceps and Wescott scissors. Subconjunctival anesthesia may be preferred by some surgeons or patients. The excised conjunctiva or other tissue is removed and then transfected either in the operating room or in an adjacent area then reimplanted in the appropriate location in the same session. Alternatively the tissue can be maintained under sterile conditions, taken to a sterile facility where transfection and subsequent subculture and testing can be performed, and reimplantation of the tissue performed one to three weeks later. A similar procedure can be performed on the sclera, except it may be preferred to use subconjunctival rather than topical anesthesia. In some instances alternative tissue substrates such as iris pigment epithelium may be substituted for conjunctiva or sclera. Although a tissue sample of any size or dimension can be removed, typically a tissue sample of approximately one cubic millimeter of tissue or less is obtained. After removal of the tissue, the site can sutured or treated as needed.

In an alternative embodiment, the tissue is harvested from a donor, rather than the patient. In this case, donor tissue would be isolated and transfected as described above for autologous transplantation. It may be transplanted after transfection in the same session, or, alternatively the tissue can be maintained under sterile conditions, taken to a sterile facility where transfection and subsequent subculture and testing can be performed, and reimplantation of the tissue performed one to three weeks later. In this case, donor tissue may be tested to determine suitability of transplantation, for example for viral or other pathogens or immunocompatibility with recipient.

Nucleic Acids

Harvested cells or tissues, cell lines made from these cells or tissues, or standard cell lines are genetically modified according to the present invention with a nucleic acid as described above. The nucleic acid may encode, for example, a therapeutic protein or an RNAi cassette, such as a shRNA. Alternatively, the nucleic acid may be used to repair or replace an endogenous gene, for example DNA used for homologous recombination, or an oligonucleotide used for gene repair. Modifications include, for example, modifying expression levels of the gene and/or replacing a mutant gene with a wild-type copy of the gene. The nucleic acid may be DNA or RNA, but is preferably DNA. Also preferably, the nucleic acid is a DNA construct, in particular a cDNA or synthetic DNA, and can be further modified to improve transcription and/or translation in the host cell, or to reduce or minimize gene silencing. The nucleic acid construct may comprise, operably linked, a promoter region, a nucleotide, and optionally, a termination signal. Preferably, this construct is part of a plasmid. Preferably, the cells or tissue are stably transfected so that the transplanted cells or tissue may act, for example, as a bio-factory to produce a therapeutic protein for a long period of time.

Multiple nucleic acid sequences can be introduced into the cells or tissue, including multiple copies of the same nucleic acid sequence and/or multiple copies of differing nucleic acid sequences encoding for different therapeutic or marker proteins. In one embodiment, each nucleic acid sequence is present on a separate polynucleotide construct, plasmid, or vector. In another embodiment, both nucleic acid sequences are present on one polynucleotide construct, plasmid, or vector, with each sequence under the control of a separate promoter. Alternatively, and in yet another embodiment, both nucleic acid sequences are present on one polynucleotide construct, plasmid, or vector, with the polynucleotide structured so that it is bicistronic and where both nucleic acid sequences are under the control of a single promoter. These various embodiments are further described below.

With respect to the embodiments where two differing nucleic acid sequences are present on one polynucleotide construct, plasmid, or vector, each sequence can be under the control of a separate promoter or can be under the control of a single promoter. In addition to a first nucleic acid sequence encoding for a selected therapeutic protein, in this embodiment, a second nucleic acid sequence encoding, for example, a second therapeutic protein or a marker is included in the construct. Expression of this gene may be constitutive; in the case of a selectable marker this may be useful for selecting successfully transfected cells or for selecting cells or transfected populations of cells that are producing particularly high levels or optimal therapeutic levels of the protein. It will also be appreciated that a selectable marker may be used to provide a means for enriching for transfected cells or positively selecting for those cells which have been transfected, before reintroducing the cells into the patient, as will be described below.

Markers may include selectable drug resistance genes, metabolic enzyme genes, fluorescent proteins, bioluminescent proteins, or any other markers known in the art. Exemplary fluorescent proteins include, but are not limited to: green fluorescent protein, cyan fluorescent protein, yellow fluorescent protein, DsRed fluorescent protein, AsRed fluorescent protein, HcRed fluorescent protein, and maxFP-green protein. When a marker gene is included in the vector construct, it will be appreciated that the marker can be used to quantify the amount of fluorescence after transfection and/or before transplantation and/or after transplantation. Quantitative determination of fluorescence can be undertaken after transfection but before transplanting the tissue using, for example, fluorescence microscopy, flow cytometry, or fluorescence-activated cell sorting (FACS) analysis, in order to quantify the expression of fluorescence markers ex vivo. After transplanting the tissue, in vivo monitoring of the extent of fluorescence, as a measure of production of the therapeutic protein, can be done by examining the patient with a fluorescent ophthalmoscope or a surgical microscope equipped for fluorescence imaging, and can be documented with a CCD camera. It will be appreciated that the marker gene can be used to indicate levels of transgene expression and can be monitored by a non-invasive or a minimally invasive procedure. If marker gene expression decreases, another tissue implant can be inserted into the patient to increase the level of therapeutic protein. By using a marker gene, diminished expression of the therapeutic protein can be recognized early, rather than waiting until decreased levels of the therapeutic gene lead to disease progression.

It will be evident that for many gene therapy applications, selection for expression of a marker gene may not be possible or necessary. Also, it is possible that for in vivo applications, vectors without any internal promoters may be preferable. Single transcription unit vectors, which may be bi-cistronic or poly-cistronic, coding for one or two or more therapeutic genes, may be designed.

Where two or more genes are present and under transcriptional control of a single promoter, there may be an internal ribosome entry site (IRES), e.g. from picornaviral RNA, to allow both genes to be separately translated from a single transcript. Retroviruses incorporating IRES sequences are known in the art, for example in U.S. Pat. No. 5,665,567. Briefly, in bicistronic or multicistronic vectors, the individual reading frames of the gene segments encoding the proteins lie on the transcription unit (expression unit). Expression of each cistron is effected using a single promoter, in conjunction with a specific nucleic acid sequence, typically untranslated regions of individual picorna viruses, e.g. poliovirus or encephalomyocarditis virus, or a cellular protein, e.g. BiP. In the picorna viruses, a short segment of the 5' untranslated region, the so-called IRES (internal ribosomal entry site) functions as an initiator for translation of reading frames.

Figure 7:
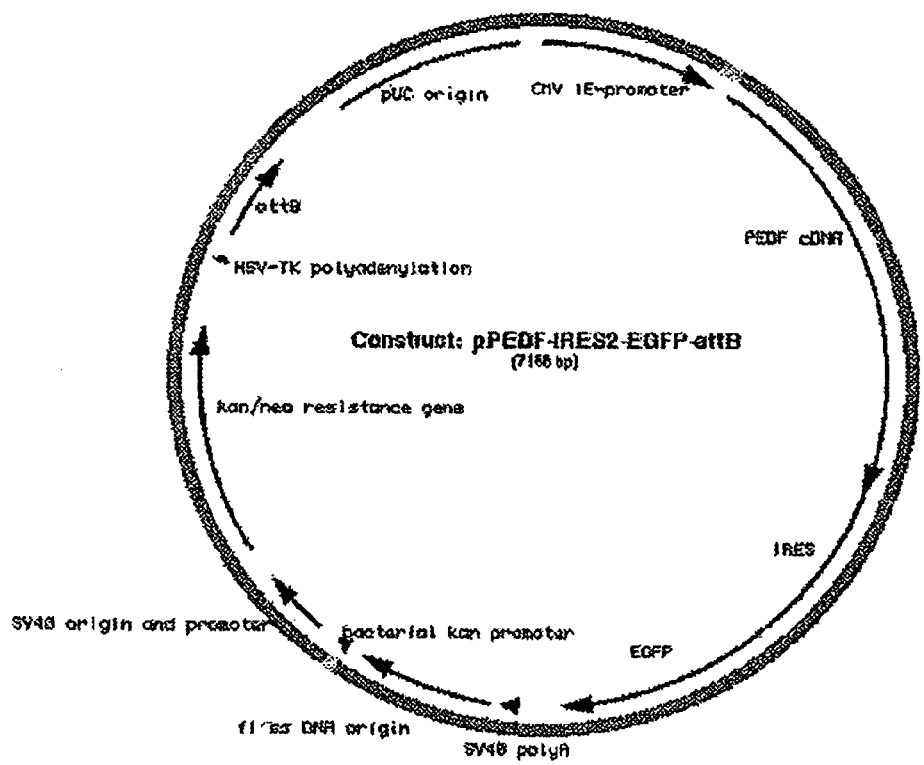
FIG. 7 shows an example of a plasmid construct suitable for gene therapy of an ocular disease according to the present invention. The plasmid contains a nucleotide sequence encoding for pigment epithelium-derived factor (PEDF) and a nucleotide sequence encoding for enhanced green fluorescent protein (eGFP) under control of a cytomegalovirus (CMV) promoter, the two sequences linked by an internal ribosome entry site (IRES) coding sequence.

By way of a specific example, and with reference to FIG. 7, the cells or tissue can be transfected with a plasmid having one promoter that drives the expression of a first therapeutic protein, such as pigment epithelium-derived factor (PEDF), and of a selectable marker, such as a fluorescent protein like enhanced green fluorescent protein (eGFP) under control of a cytomegalovirus (CMV) promoter. The CMV promoter is positioned at the 5' end of the construct. Downstream of the 3' end of the CMV promoter is the PEDF nucleotide sequence that encodes for PEDF protein. In the 3' direction of PEDF is an IRES site, which is designed to allow translation of multiple genes on an mRNA transcript. Following the IRES site in the 3' direction is the eGFP coding sequence. The IRES will allow translation of eGFP as well as translation of PEDF.

The promoter region of the construct can be chosen from among all promoter regions that are functional in mammalian cells, in particular human cells. The promoter can be a strong or weak promoter, a constitutive or a regulated/inducible promoter, a ubiquitous or selective promoter. The promoter can be of different origin such as cellular, viral, artificial, and the like. Particular types of promoters are house-keeping promoters, i.e., promoters from cellular genes expressed in mammalian tissues or cells, or viral promoters (CMV, LTR, SV40, etc.). Furthermore, the promoter region can be modified artificially to include enhancer element(s), inducibility element(s) and the like. The promoter, secretion and termination region sequences can be selected and adapted by the skilled artisan based on the polypeptide, the pathology, the vector used, etc. In this regard, the nucleic acid construct can be inserted into various kinds of vectors such as plasmids, episomes, artificial chromosomes and the like.

The nucleic acid construct can optionally include a secretion signal, positioned between the promoter and coding regions, which allows, or facilitates, the secretion of the polypeptide outside of the cells. The secretion signal may be homologous with respect to the polypeptide (i.e., from the same gene) or heterologous thereto (i.e., from any other gene encoding a secreted polypeptide, in particular a mammalian gene, or artificial). Examples of secretion signals include the signal peptide of vascular endothelial growth factor (VEGF), pre pro nerve growth sequence (NGS), and the like.

Various approaches may be used to achieve long-term expression of the nucleic acid in the cells or tissue. One approach involves a circular vector carrying a recombination site and the polynucleotide sequence encoding for the therapeutic protein, shRNA, etc., and the transfection is accompanied by introduction of a recombinase that facilitates recombination between the vector's recombination site and a second recombination site in the genome of the cell being transfected. Constructs carrying a recombination site, such as a phiC31 attB site, are described, for example, in U.S. Pat. No. 6,632,672, which is incorporated by reference herein. It will be appreciated, however, that other means for long-term gene expression are contemplated, such as the other members of the serine recombinase family, transgtrases (e.g., "Sleeping Beauty"), DNA mini-circles, plasmids optimized for minimal gene silencing, or the use of a stable extrachromasomal vector such as EBV. When using a phiC31 attB recombination site, the nucleic acid constructs are comprised of the phiC31 integrase system (described in U.S. Pat. Nos. 6,632,672 and 6,808,925, which are incorporated by reference herein) to achieve site-specific integration into a target genome of interest.

Bacteriophage phi-C31 integtrase recognizes pseudo-recombination sites present in eukaryotic cells. For genetic manipulation of a eukaryotic cell, phiC31 integrase and a vector carrying a phiC31 wild-type recombination site are placed into the cell. The wild-type recombination sequence aligns itself with a sequence in the eukaryotic cell genome and the phiC31 integrase facilitates a recombination that results in integration of a heterologous gene into the eukaryotic genome. It is contemplated that any attB site, any attP site, or any pseudo att site is present on any nucleotide sequence used to introduce genetic material into the genome of the harvested or cultured cells.

Accordingly, in one embodiment, the method of integrating a polynucleotide sequence into a genome of a cell comprises introducing into the cell (i) a circular targeting construct, comprising a first recombination site and a polynucleotide sequence of interest, and (ii) a phiC31 integrase, native or modified, wherein the genome of the cell comprises a second recombination site (ie. a pseudo att site) native to the human genome. Recombination between the first and second recombination sites is facilitated by the site-specific integrase.

The therapeutic gene and the attB sequence are preferably introduced into the target cell as circular plasmid DNA. The integrase may be introduced into the target cell (i) as DNA encoding the integrase on a second plasmid, (ii) mRNA encoding the integrase, or (iii) in polypeptide form. Once phiC31 is introduced into the cell, the cell is maintained under conditions that allow recombination between the first and second recombination sites and the recombination is mediated by the phiC31 integrase. The result of the recombination is site-specific integration of the polynucleotide sequence of interest in the genome of the cell.

By way of a specific example, and with reference again to FIG. 7, a plasmid is constructed having a cytomegalovirus (CMV) promoter that drives the expression of a therapeutic protein, pigment epithelium-derived factor (PEDF), and as a marker, enhanced green fluorescent protein (eGFP). In the 3' direction of the PEDF nucleotide sequence is an IRES site, followed in the 3' direction by the eGFP coding sequence. The IRES allows translation of eGFP as well as translation of PEDF. The plasmid, which also includes an attB nucleic acid sequence, is detailed in Example 1 and the plasmid sequence is identified herein as SEQ ID NO: 1.

Transfection of a wide variety of genes encoding for therapeutic proteins is contemplated, and preferred candidate genes include genes that encode for diffusible proteins that act extracellularly to have a therapeutic effect. In a preferred embodiment, a nucleic acid sequence coding for a protein with anti-angiogenic activity or with neurotrophic activity is transfected into human cells. Exemplary proteins include, but are not limited to, pigment epithelium-derived factor (PEDF), truncated soluble VEGF receptor sFlt-1, truncated soluble VEGF receptor sFlk-1, VEGFR-1, VEGFR-2, angiostatin, endostatin, tissue inhibitor of metalloprotease 3 (TIMP-3), ExTek, ciliary neurotrophic factor (CNTF), brain-derived neurotrophic factor (BDNF), bone morphogenetic protein 4 (BMP4), alpha fibroblast growth factor (aFGF), beta fibroblast growth factor (bFGF), and any protein having activity on or within the compliment factor H pathway. Preferred biologically active polypeptides exhibit neurotrophic and/or anti-angiogenic activity. The most preferred biologically active polypeptides are autogenic and thus do not invoke an immune response in the subject or are known in the art not to invoke an immune response.

In a preferred embodiment, human cells are genetically modified to contain a recombinant nucleic acid construct that directs the cells to produce the therapeutic protein encoded by the recombinant nucleic acid. The cells can be immediately transplanted into the subject or can be cultured in vitro for a period of time. In a preferred embodiment, mammalian cells modified with a vector containing at least one nucleic acid sequence coding for a therapeutic protein and another nucleic acid sequence coding for a marker gene are prepared for transplantation. When the cells are cultured in vitro prior to transplantation, a selection step can be performed in order to isolate the cells that effectively contain the recombinant nucleic acid construct and express the polypeptide. The selection step will depend in part on the marker gene and can involve measuring fluorescence, screening for antibiotic resistance, or the like. Cells expressing the marker gene are selected for transplantation. In general, when the cells are cultured for a period of time after transfection, the treatment method is performed on a subject over more than one visit to the medical provider. In a first visit, the tissue is harvested. The tissue cells are transfected and cultured in vitro, during which time the level of expression can be monitored and stably-transfected cells from the tissue selected, by, for example, quantifying expression of a marker or of the desired protein by methods noted above for measuring marker expression, for transplantation. The subject returns to the medical provider for a second visit during which the transfected tissue is transplanted.

Alternatively, tissue can be obtained, transfected, and transplanted during a single patient visit to a medical provider. In this scenario, the level of expression of a marker or the desired therapeutic protein can be monitored in vivo, by methods mentioned above, such as ophthalmoscope or a surgical microscope.

In a preferred embodiment, one or more nucleotide sequences coding for a therapeutic protein and one nucleotide sequence coding for a marker gene are present in the same polynucleotide vector construct. The marker gene is coupled to the therapeutic gene by an IRES sequence. Quantification of the degree of fluorescence emitted from a cell or group of clonal cells would correlate with the amount of expression of the therapeutic protein, enabling selection of stably transfected cells or monitoring of protein expression after transplantation.

Transplantation

Figure 8:
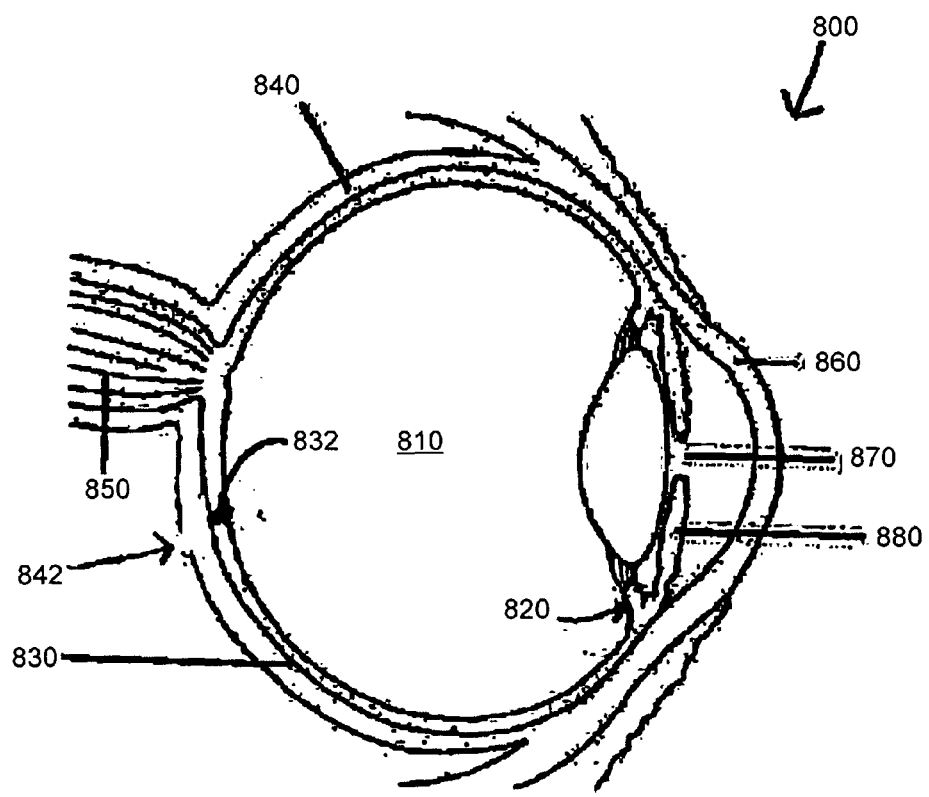
FIG. 8 shows ocular regions suitable for transplantation according to the present invention.

The transfected tissue or cells can be transplanted into the subject in any of a number of different implantation sites in or near the eye by a provider of medical care. FIG. 8 is a diagram showing an eye 800 in cross-sectional view, and indicating some of the preferred sites for placing genetically modified cells or tissue into the patient. Identified anatomical features are retina 830, sclera 840, optic nerve 850, cornea 860, pupil 870 and iris 880. Sites in eye 800 preferred for implanting the transfected cells or tissue include the vitreous humor 810, near the pars plana 820, near the posterior retina 832, or sub-sclerally 842. Other sites for implanting tissue, which are not specifically indicated in FIG. 8, include the choroid, retinal pigment epithelium (RPE), and near the macula epi-retinally, sub-retinally, or intra-retinally.

In a preferred embodiment, the transfected cells or tissue are implanted into the subject in the absence of an encapsulating member, such as a polymer capsule or a so-called "cage". Especially in the case where the method described herein employs autologous tissue or cells, encapsulation of the tissue or cells within a cage is not necessary for immunosuppression.

However, encapsulation could be used to enhance graft survival and/or to reduce possible splintering of cells away from the graft to other sites in the eye. A number of cage designs have been proposed for ophthalmologic use for various purposes, as described in U.S. Pat. Nos. 6,500,449 and 6,663,894. The cage would be able to house the tissue or cell transplant and would have pores large enough for proteins to diffuse out, but small enough so that cells could not enter or leave. The cage may contain a matrix or other materials to support cell survival and cell anchoring to prevent cell migration to other sites.

EXAMPLES

The following examples are illustrative in nature and are in no way intended to be limiting.

Example 1

Construction of a Plasmid for Transfection

The plasmid shown in FIG. 7 contains the sequence SEQ ID NO: 1. SEQ ID NO: 1 includes a cytomegalovirus (CMV) promoter (1-589 bp), a nucleotide sequence encoding for pigment epithelium-derived factor (PEDF; 590-2131 bp), an internal ribosome entry site (IRES) coding sequence (b2151-2735 bp), and a nucleotide sequence encoding for enhanced green fluorescent protein (eGFP; bp 2739-3455), an SV40 polyA sequence (3612-3662 bp), a phi C31 attB site (3952-4245 bp), a bacterial kan promoter (4541-4576 bp), SV40 origin and promoter enhancer (4653-4955 bp), neo for G418 selection (5004-5798 bp), and an pUC origin (6383-7026 bp).

To make this plasmid, begin with vector pIRES-EGFP, commercially available from Clontech. Cut the vector with the restriction enzyme BsaI (New England Biolabs) to linearize the vector, make blunt ends (e.g., using DNA Polymerase I, Large (Klenow) Fragment, New England Biolabs), and treat with a phosphatase to remove the phosphate groups (e.g., using calf intestinal phosphatase, New England Biolabs). Ligate this vector to the fragment containing attB when pTA-attB+ is cleaved with EcoRJ and then its ends blunted, to form the plasmid pIRES-EGFP-attB.

In the second cloning step, use PCR amplification with primers designed to amplify the PEDF gene from human cDNA. Cleave pIRES-EGFP-attB with the restriction enzyme SmaI, which linearizes the plasmid upstream of the IRES sequence and use a phosphatase to remove the phosphate groups. Ligate the PCR-amplified fragment into the vector to form the plasmid pPEDF-IRES-GFP-attB, shown in FIG. 7.

Example 2

Transfection of Conjunctival Tissue with Luciferase Gene

A study was conducted in support of the method described herein, where a luciferase marker gene was transfected into conjunctiva tissue. Conjunctival tissue was explanted from adult New Zealand White rabbits and placed in tissue culture dishes. All samples were placed in 1 mL phosphate buffered saline solution with 100 micrograms of plasmid DNA encoding the luciferase gene under a CMV promoter. All samples were cultured in Dulbecco's Modified Eagle Medium (DMEM) plus 10% serum and antibiotic/antimicotic for 24 hours after transfection. Samples were then treated with luciferin substrate (150 micrograms luciferin per ml medium) and imaged using the IVIS-200 system (Xenogen Corp.).

Figure 9:
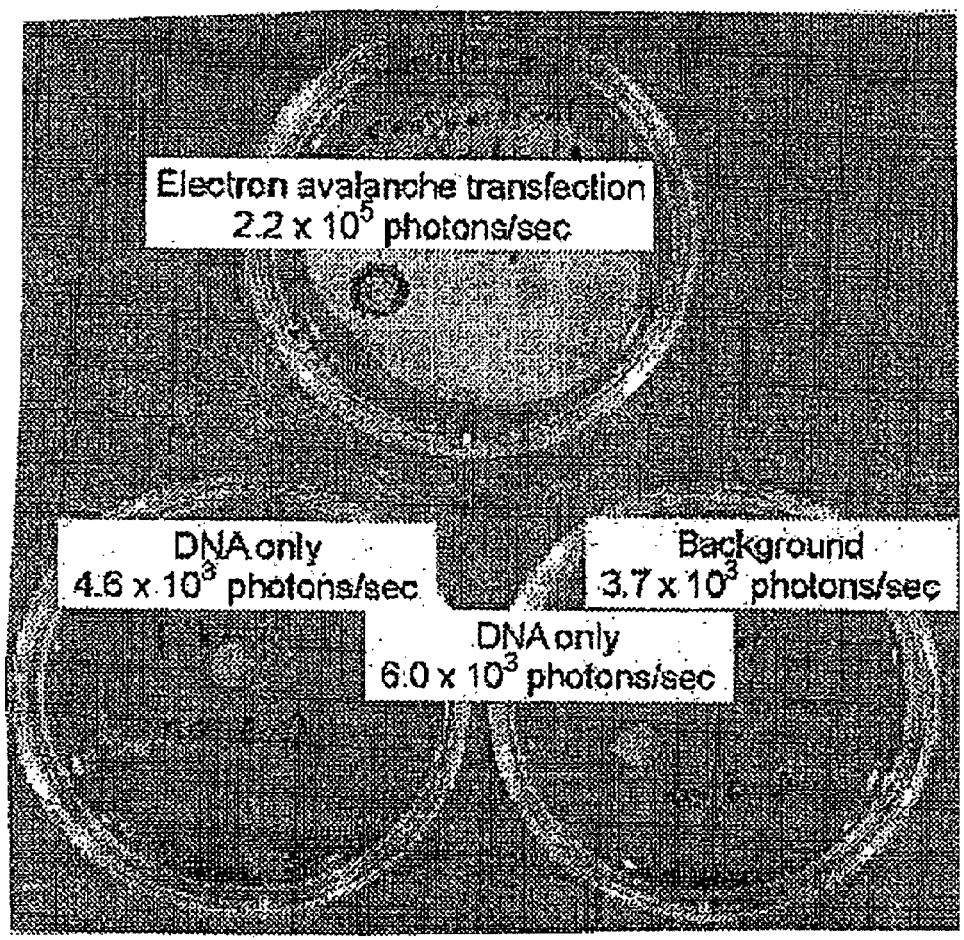
FIG. 9-10 show examples of electron avalanche-mediated transfection according to the present invention.

The conjunctival tissue, which contained conjunctival fibroblasts, was transfected using electron-avalanche mediated transfection with a luciferase marker gene. A control sample of tissue was contacted with the luciferase gene in the absence of electron-avalanche mediated transfection. Twenty-four hours after transfection, bioluminescence was measured. As shown in FIG. 9, the tissue transfected with electron-avalanche mediated transfection emitted $2.2 \times 10^5$ photons/sec, two orders of magnitude higher than the cells transfected in the absence of the electron-avalanche mediated transfection ($4.6 \times 10^3$ photons/sec). Background emission was measured at $3.7 \times 10^3$ photons/sec.

Example 3

Comparison of Electron Avalanche Versus Traditional Electroporation in DNA Transfer Because electroporation protocols vary for different tissues, experiments were first conducted to determine the optimal protocol for transfecting CAM from a developing chicken egg using traditional electroporation. CAM is a live, readily available, and inexpensive tissue. Its epithelial layer is uniform and has high resistance, making it a good model for epithelial cell layers, such as retinal pigment epithelium. In this model system, 100 µg of pNBL2 plasmid DNA encoding the luciferase gene was pipetted onto the CAM, and pulses were applied. Specifically, a 250-µs, 150-V phase, followed by a 5-ms, 5-V phase in the same polarity was applied. Optimal results were achieved with 50 cycles applied at 1 Hz. The tissue was then cultured and assayed for luciferase bioluminescence. Luciferase expression using this method was about $10^4$ photons/s.

Figure 10:
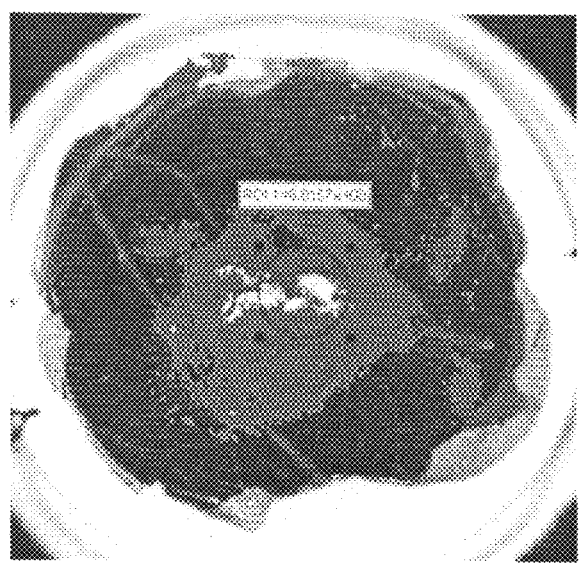

For electron-avalanche transfection, a 50-µm wire microelectrode 1 mm in length was used to apply a series of symmetric biphasic pulses, with each phase 250 µs in duration and 600 V in amplitude. The microelectrode was scanned over a 4-mm² area, and approximately 50 pulses were applied. As shown in FIG. 10, the resultant luciferase expression was about $10^9$ photons/s, 10,000-fold higher than levels seen with conventional electroporation.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A method of delivering a nucleic acid to an ocular region of a subject, comprising:
providing a nucleic acid and target cells or target tissue, the target cells being an autologous or allogeneic cell line or being isolated from an autologous or allogeneic individual and the target tissue being from an autologous or allogeneic individual;
applying a voltage of about 100 V to about 10 kV for a duration of about 20 μsec to about 100 msec to an electrode to generate both an electric field and a mechanical stress wave, the electrode positioned to provide both the electric field and the mechanical stress wave to the target cells or target tissue sufficient to transfect the nucleic acid into the cells or the tissue; and
transplanting the transfected cells or the transfected tissue into an ocular region of the subject,
wherein the nucleic acid is expressed in the ocular region.

2. The method of claim 1, wherein generating both the electric field and the mechanical stress wave comprises forming a plasma discharge.

3. The method of claim 1, further comprising isolating the cells or the tissue from the subject before transfection.

4. The method of claim 1, further comprising culturing the cells or the tissue prior to transplanting the transfected cells or the transfected tissue.

5. A method of delivering a nucleic acid to an ocular region of a subject, comprising:
placing an electrode at a target tissue within the ocular region of the subject;
providing a nucleic acid to the target tissue; and
applying voltage of about 100 V to about 10 kV for a duration of about 20 μsec to about 100 msec to the electrode to form a plasma discharge,
the electrode providing both an electric field and a mechanical stress wave to the tissue sufficient to deliver the nucleic acid into the tissue.

6. The method of claim 1, wherein the cells or the tissue originate from the ocular region of the individual.

7. The method of claim 6, wherein the cells or the tissue is conjunctival fibroblasts, scleral cells, epithelial cells, or cells of the ciliary body or ciliary muscle.

8. The method of claim 1, wherein the subject has a condition selected from the group consisting of age-related macular degeneration, choroidal neovascularization, retinal degeneration, glaucoma, diabetic retinopathy, and retinal dystrophies.

9. The method of claim 1, wherein the cells or the tissue are transplanted by placing the cells or the tissue in an implantable device, and implanting the device within an ocular region of the subject.

10. The method of claim 1, wherein the nucleic acid is DNA.

11. The method of claim 1, wherein the nucleic acid encodes a therapeutic protein or shRNA.

12. The method of claim 5, wherein the target tissue comprises conjunctival fibroblasts, scleral cells, epithelial cells, or cells of the ciliary body or ciliary muscle.

13. The method of claim 5, wherein the subject has a condition selected from the group consisting of age-related macular degeneration, choroidal neovascularization, retinal degeneration, glaucoma, diabetic retinopathy, and retinal dystrophies.

14. The method of claim 5, wherein the nucleic acid is expressed in the ocular region.

15. The method of claim 5, wherein the nucleic acid is DNA.

16. The method of claim 5, wherein the nucleic acid encodes a therapeutic protein or shRNA.

17. The method of claim 1, wherein the voltage is about 100 V to about 1 kV.

18. The method of claim 1, wherein the duration of the voltage pulse is about 20 μsec to about 1 msec 19. The method of claim 5, wherein the voltage is about 100 V to about 1 kV.

20. The method of claim 5, wherein the duration of the voltage pulse is about 20 μsec to about 1 msec.

* * * * *